United States Patent [19]

Dobrescu et al.

[11] 4,053,584

[45] Oct. 11, 1977

[54] PRE-FARROWING PREGNANT SOW PIGLET COLIBACILLOSIS VACCINES AND PROCESS FOR THEIR ADMINISTRATION TO PREGNANT SOWS BEFORE FARROWING

[75] Inventors: Lucia Dobrescu, Brussels; Constant Huygelen, Huldenberg, both of Belgium

[73] Assignee: Recherche et Industrie Therapeutiques, Belgium

[21] Appl. No.: 671,463

[22] Filed: Mar. 29, 1976

Related U.S. Application Data

[63] Continuation of Ser. No. 549,237, Feb. 12, 1975, abandoned, which is a continuation-in-part of Ser. No. 311,998, Dec. 4, 1972, abandoned.

[51] Int. Cl.² .................... A61K 39/02; A61K 39/40
[52] U.S. Cl. .................................... 424/92; 424/87
[58] Field of Search .................... 424/87, 92

[56] References Cited

U.S. PATENT DOCUMENTS

| | | | |
|---|---|---|---|
| 3,075,883 | 1/1963 | Scherr et al. | 424/88 |
| 3,127,318 | 3/1964 | Eversole et al. | 424/92 |
| 3,149,036 | 9/1964 | Woodhour et al. | 424/88 |
| 3,376,198 | 4/1968 | Petersen et al. | 424/88 |

FOREIGN PATENT DOCUMENTS

| | | | |
|---|---|---|---|
| 277,937 | 5/1964 | Australia | 424/88 |
| 1,152,607 | 5/1969 | United Kingdom | 424/88 |

OTHER PUBLICATIONS

Miniats et al., Can. Vet. J., 8:260–268 (1967) "Antibody Response of Young Pigs to Vaccination with *E. Coli*".
Kohler et al., Am. J. Vet. Res., 29:1419–1428 (July, 1968) "Serological Response of Swine to Escherichia Coli Antigens".
Sojka, Vet. Bull., 41(7):509–522 (July, 1971) "Entoric Diseases in New-Born Piglets, Calves and Lambs due to *Escherichia Coli Infection*".
Smith, et al., J. Med. Microbiol, 3:387–401 (1970) "The Relationship between Two Apparently Different Enterotoxins Produced by Enteropathogenic Strains of *Escherichia Coli of Porcine Origin*".
Gyles et al., J. Infect. Diseases, 120(4):419–426 (Oct. 1969) "A Heat-Labile Enterotoxin from Strains of *Escherichia Coli Enteropathogenic for Pigs*".

*Primary Examiner*—Shep K. Rose
*Attorney, Agent, or Firm*—Janice E. Williams; William H. Edgerton; Alan D. Lourie

[57] ABSTRACT

Piglet colibacillosis vaccine for intramuscular or subcutaneous administration to pregnant sows comprising cell-free heat labile (LT) *E. coli* enterotoxin with an adjuvant and the method for preventing piglet colibacillosis consisting in administering said vaccine to pregnant sows from 3 to 6 weeks before farrowing.

8 Claims, No Drawings

PRE-FARROWING PREGNANT SOW PIGLET COLIBACILLOSIS VACCINES AND PROCESS FOR THEIR ADMINISTRATION TO PREGNANT SOWS BEFORE FARROWING

This is a continuation of application Ser. No. 549,237 filed Feb. 12, 1975, now abandoned which is a continuation-in-part of Ser. No. 311,998, filed Dec. 4, 1972, now abandoned.

This invention relates to new colibacillosis vaccines, more particularly vaccines against piglet colibacillosis.

Neonatal colibacillosis of swine is an important cause of death in piglets and numerous attempts have been made to control this illness by actively immunizing the dam against *Escherichia coli* (*E.dcoli*) either by killed or live vaccines or by giving the pigs *E. coli* antiserum.

Active immunization of the sows has been performed by parenteral administration of *E. coli* vaccines (see for instance M.R. Wilson and J. Svendsen. Amer. J. Vet. Res. 32, 1971, 891–898) but because the *E. coli* strain or strains used for immunization may only generate specific antibodies while there may be several and different strains associated with a given outbreak, these attempts at prophylaxis based on antibacterial immunity have given inconsistent and generally unsatisfactory results. Even if in some cases good protection was obtained, it was restricted to those serotypes of *E. coli* present in the vaccine.

Administration of antiserum (see for instance O.P. Miniats, Can. Vet. J. 11, 1970. 52–56) cannot constitute an practical prohylactic means against piglet colibacillosis. The protection afforded by administration of antiserum indeed is of short duration and requires continuous administration to the piglets.

We have now surprisingly found that when administering to pregnant sows from 3 to 6 weeks before farrowing heat labile (LT) *E. coli* enterotoxin with an adjuvant instead of administering whole cells of *E. coli*, the vaccinated sows not only develop antibodies in their colostrum and milk but also protect therethrough the piglets against the action of enterotoxins produced by *E. coli* serotypes either homologous or heterologous to the *E. coli* strain from which the heat labile (LT) enterotoxin was isolated.

In other words, the administration of the heat labile (LT) *E. coli* enterotoxin to the dam does protect the piglets not only against colibbacillosis due to the heat labile (LT) *E. coli* enterotoxin but also against colibacillosis due to the heat stable (ST) enterotoxin.

It is thus the object of the present invention to afford a method of protection of piglets against colibacillosis, said method consisting in administering to the sows and with an adjuvant a heat labile (LT) *E. coli* enterotoxin preparation isolated from a culture of an enteropathogenic *E. coli* serotype.

The said heat labile (LT) *E. coli* enterotoxin preparation can be isolated from any *E. coli* serotype susceptible to provoke piglet colibacillosis and containing necessarily the heat labile (LT) *E. coli* enterotoxin. An example of such *E. coli* serotype is *E. coli* strain ATCC 21972, but many other examples of *E. coli* strains containing the LT enterotoxin have been cited in the literature, e.g. by W.J.Sojka in Annales De Medecine Veterinaire 116 : 377–446, 1972 listing *E. coli* strains G 7, G 205, G 4/66, G 491, E 68 type I, G 1253 and *Abbotstown;* by E.M-.Kohler in Ann. N.Y. Acad. Sci. 176 : 212–19, 1971 listing *E. coli* strains Arnold, Emery, 263, 407 and P 307, by H.W. Smith and C.L. Gyles in J. Med. Microbiol, 3 : 387–401, 1970 referring to 25 *E. coli* strains showing different serotypes, by L. Dobrescu & al. in Zentrablbl. Vet. Med. (B) 20 : 222–29, 1973 listing 4 *E. coli* strains freely obtained without restriction from Institut National de Recherches Veterinaires, Brussels (Belgium), Faculty of Veterinary Medicine, University of Ghent (Belgium) and Veterinaruntersuchungs-und-Tiergesundheitsamt, Dresden (E. Germany).

The procedure for isolating the heat labile (LT) *E. coli* enterotoxin is well known. It has been described by GYLES and BARNUM (J. Infect. Dis. 120, 1969, 419-26) and variations of this procedure have been described e.g. by H.W. Smith and C.L. Gyles (J. Med. Microbiol, 3, 1970, 387–401), H.W. Smith and S. Halls (J. Path. Bact. 93, 1967, 531–43) and M.R. Wilson, C. Gyles and J. Svendsen (Can. J. Comp. Med. 35, 1971, 294–97).

Any of these procedures as well as any other equivalent known by those skilled in the art may be used for the purpose of preparing the heat labile (LT) *E. coli* enterotoxin isolate which is employed in the present invention.

This invention does not require to get pure heat labile (LT) *E. coli* enterotoxin but purification can be eventually obtained e.g. either by electrophoresis or density gradient ultracentrifugation or adsorption/elution from hydrophilic cross-linked dextrans such as Sephadex (a product manufactured and sold by Pharmacia Fine Chemicals AB, Uppsala 1, Sweden).

Essentially the invention only requires that the enterotoxin be liberated and separated from the cells of *E. coli* and substantially free from lipopolysaccharides.

The adjuvant —the role of which is to assure high immune response— may be any product or composition selected from the group consisting of aluminium hydroxide and aluminium phosphate such as for instance ALHYDROGEL (tradename of an aluminium hydroxide gel manufactured and sold by SUPERFOS Export C°, Copenhagen, Denmark) on which the enterotoxin can be adsorbed up to saturation and preferably at the saturation, and water-in-oil emulsions such as adjuvant 65 (a water-in-oil emulsion of antigen in peanut oil emulsified by the addition of mannide monooleate and stabilized by the addition of aluminium monostearate) or complete FREUND's adjuvant (a water-in-oil emulsion of light mineral oil emulsified with mannide monooleate and supplemented with killed Mycobacterium tuberculosis).

The enterotoxin/adjuvant ratio is depending on the nature of the adjuvant as well known by the art. For instance, for Freund complete adjuvant, a volume of adjuvant substantially equal to the volume of antigen suspension is employed (see Handbook of experimental immunology 1967 Ed. by D.M. Weir, Blackwell Scient. Public, p. 850–51; 1208–09). For aluminium hydroxide or phosphate, the adjuvant character of which is due to their adsorption capacity, the enterotoxin/adjuvant ratio is calculated for maximum adsorption of the enterotoxin on the adjuvant (see symp. Series Immunobiol. Standard 6 : 173–80, 1967).

According to this invention, an effective amount of the heat labile (LT) *E. coli* enterotoxin preparation with the adjuvant is administered to pregnant sows by intramuscular or subcutaneous route. The dosage unit is at least 5 mg. and preferably from 10 to 150 mg (dry weight basis).

The following examples illustrate the present invention; they should not be constructed as limiting its scope.

EXAMPLE 1

Production medium (solid)

Water (10 liters) is added to 130 g. of BACTOTRYPTOSE broth and 150 g. of BACTO-AGAR (BACTO-TRYPTOSE and BACTO-AGAR are trade names of products manufactured and sold by DIFCO Laboratories, Detroit 1, Mich., U.S.A.). The mixture is heated with stirring up to 121° C for 60 minutes. Twenty g. of BACTO-DEXTROSE (trade name of a product manufactured and sold by DIFCO Laboratories) are dissolved in 20 ml. of distilled water and the solution is passed through a 0.45 micron Millipore sterilizing filter (Millipore Corporation, Bedford, Mass., U.S.A.). Both preparations are then pooled and 100 ml. aliquots are distributed into 500 square centimeter Roux flasks.

Seed Preparation

*E. coli* strain ATCC 21972 is re-hydrated with sterile saline and incubated for 18 hours at 37° C in Petri dishes containing each 20 ml of TRYPTOSE-AGAR solid-medium prepared by mixing 26 g. of TRYPTOSE broth, 30 g. of AGAR DIFCO (TRYPTOSE broth and AGAR DIFCO are products manufactured and sold by DIFCO Laboratories) up to one liter with water, the mixture being heated for 45 minutes at 115° C.

A liquid culture medium (named pp$_3$) is then prepared as follows : Proteose peptone N° 3 (a product manufactured and sold by DIFCO Laboratories) 30 g., yeast extract (4 g.) and dextrose (5 g.) are dissolved in 1 liter of water at 60° C. After cooling, NaCl (5 g.), NaHPO$_4$ (5.05 g.) and KH$_2$PO$_4$ (1.2 g.) are added thereto. The medium, the pH of which is 6.9–7.0 is filtered on Seitz EKS filter and distributed into 100 ml. culture flasks.

These culture flasks are inoculated with the smooth colonies obtained on Petri dishes, using one colony per 20 ml. of PP$_3$ liquid medium and incubated for 6 hours at 37° C with shaking one rocking shelves (22 to 24 rockings per minute).

*E. coli* production

Four milliliter aliquots of the obtained *E. coli* culture in PP$_3$ liquid medium (i.e. about 4.10$^9$ bacteria) are inoculated in each 500 square centimeter Roux flasks containing the production medium which are then incubated for 1 day at 37° C with shaking one rocking shelves (22 to 24 rockings per minute). Each cell culture is harvested in 25 ml. of distilled water and the harvests of 15 Roux flasks (one series) are pooled in 1 liter flasks. A sample (1 ml.) is taken from each series for purity testing.

Therefoere, 0.5 ml. is seeded on TRYPTOSE-AGAR broth in Petri dishes and incubated for 7 days at 34° C and the other 0.5 ml. fraction is seeded in Petri dishes containing 20 ml. of Sabouraud dextrose agar prepared by dissolving 65 g. of Sabouraud dextrose agar DIFCO (a product manufactured and sold by DIFCO Laboratories) in 1 liter of hot distilled water and further sterilized and the culture are incubated for 7 days at 22° C.

The harvests are supplemented with a sterile 1 percent neomycin sulfate aqueous solution (1.2 ml. of neomycin sulfate solution per 100 ml. of harvest) and the cells are disrupted by sonicating the medium for 30 minutes in a Branson Europa sonicator model J 22 (Branson Europa N.V., Soest, The Netherlands), the medium being maintained in a melting ice bath.

After disruption of the cells, of suspension is centrifuged for 2 hours at 2,550 r.p.m. at the temperature of 5° C in order to eliminate the cell debris.

The supernatant fluid is successively passed through a clarifying filter and through a 0.45 micron Millipore sterilizing filter (Millipore is a trademark of Millipore Corporation, Bedford, Mass., U.S.A.).

Ammonium sulfate previously sterilized by ethylene oxide is added to the filtrate up to reaching 50 % saturation (380 g. of ammonium sulfate per liter of filtrate) and the mixture is allowed to stand for 3 hours at room temperature. The obtained precipitate is centrifuged for 2 hours at 2,550 r.p.m. at the temperature of 5° C.

The sediment is poured into a cellophane bag and dialyzed against running water until the concentration in ammonium sulfate is lowered between 0.1 and 0.01 %, the ammonium sulfate contents being tested with Nessler's reagent.

The enterotoxin preparation is sterilized by passage through a 0.45 micron Millipore sterilizing filter (Millipore is a trademark of Millipore Corporation) and freeze-dried.

EXAMPLE 2

A 1 g. aliquot of freeze-dried enterotoxin preparation obtained at the end of example 1 is rehydrated by adding thereto 20 ml. of a sterile phosphate buffer saline (pH 7.4) consisting of NaCl (8 g.), KCl (2 g.), Na$_2$HPO$_4$(11.5 g). KH$_2$PO$_4$ (2 g.), CaCl$_2$.2H$_2$O (1.325 g.), MgCl$_2$.6H$_2$O (1 g.) and distilled water (10 l.).

The obtained vaccine is thoroughly mixed in sterile conditions with 20 ml. of sterile complete FREUND's adjuvant (i.e. a water-in-soil emulsion of light material oil emulsified with mannide monooleate and supplemented with killed *Mycobacterium tuberculosis*) and the so-obtained adjuvanted vaccine is distributed into 4 ml. vials which are either sealed or tightly stopped in order to obtain an (LT) enterotoxin amount corresponding to 100 mg. of freeze- dried preparation per vial.

The contents of each vial corresponds to one vaccine dosage unit. The vaccine is administered to pregnant sows by intramuscular or subcutaneous route from 3 to 6 weeks before farrowing.

Alternatively, the adjuvanted vaccine is distributed into larger vials in order to obtain integers of the dosage unit amount to constitute corresponding multi-doses vaccine preparations.

EXAMPLE 3

The technique is that described in example 1 up to and including the incubation of *E. coli* ATCC 21972 for 6 hours at 37° C in PP$_3$ liquid medium.

Production of *E. coli* is then carried out in a liquid production medium as follows :

Six milliliters aliquots of the so-obtained *E. coli* (i.e. about 6.10$^9$ bacteria) are inoculated in production flasks containing 300 ml. of PP$_3$ liquid medium and the culture as incubated for 1 day with shaking on rocking shelfs (22 to 24 rockings per minute).

The harvests of five production flasks (one series) are pooled and each series of harvests is centrifuged for 2 hours at 2,550 r.p.m., thesediment is re-suspended in 150 ml. of distilled water and a sample of the suspension is tested for purity as indicated in example 1.

The cell suspension is sonicated for 30 minutes in a Branson Europa sonicator model J 22, the medium being maintained in a melting ice bath.

After disruption of the cells, the suspension is centrifuged for 2 hours at 2,550 r.p.m. at 5° C in order to eliminate the cell debris. The supernatant is passed through a 0.45 micron Millipore sterilizing filter (Millipore is a trademark of Millipore Corporation) to yield 100 ml. of filtrate, the pH of which is adjusted to 6.4 with normal hydrochloric acid. Thiomersal is added in a final concentration of 0.02 %.

EXAMPLE 4

Forty milliliters of a 2 % aqueous solution of ALHYDROGEL (a product manufactured and sold by SUPERFOS EXPORT Company) is thoroughly mixed with 80 ml. of the filtrate obtained at the end of example 3, the adsorption of the enterotoxin on the ALHYDROGEL being checked by precipitation test with trichloroacetic acid.

Twenty milliliters of the supernatant fluid is discarded and the remaining mixture is distributed into 10 (10 ml.) vials which are stoppered.

The contents of each vial (9 ml.) corresponds to one vaccine dosage unit of 100 mg. (dry weight basis) of heat labile (LT) E. coli enterotoxin.

The vaccine is administered to pregnant sows by intramuscular or subcutaneous route from 3 to 6 weeks before farrowing.

Alternatively, the adjuvanted vaccine is distributed into larger vials in order to obtain integers of the dosage unit amount to constitute corresponding multi-doses vaccine preparations.

EXAMPLE 5

The technique is that of example 3 but the mixture is distributed into 100 glass vials which are stoppered.

The contents of each vial (0.9 ml.) corresponds to one vaccine dosage unit of 10 mg. (dry weight basis) of heat labile (LT) E. coli enterotoxin extract.

The vaccine is administered to pregnant sows by intramuscular or subcutaneous route from 3 to 6 weeks before farrowing.

EXAMPLE 6

Prevention of piglet colibacillosis by subcutaneous administration of heat labile (LT) E. coli enterotoxin preparations according to the invention has been demonstrated by the following trials I, II and III.

In each of these trials, the sows were vaccinated from 3 to 6 weeks before farrowing and one sow was used as control. Twenty-four hours after birth, the piglets were challenged with 400 mg. per kg. of weight of LT E. coli enterotoxin prepared according to example 1, using a stomach tube for the administration.

For three litters —as indicated in the following Tables— some piglets were also challenged with heat stable (ST) E. coli enterotoxin obtained from strain ATCC 21972, using therefore 660 mg. of ST enterotoxin.

Clinical evolution of the piglets was regularly followed regarding appearance of typical symptoms of colibacillosis.

In the following Tables:

Vaccine A represents the vaccine of example 2 at the 100 mg. (dry weight basis) dosage unit;

Vaccine G represents the vaccine of example 4 at the 100 mg. (dry weight basis) dosage unit;

Vaccine C represents the vaccine of example 5 at the 10 mg. (dry weight basis) dosage unit.

TABLE 1

| SOW N° | Vaccinated with | PIGLET N° | Challenged with | Diarrhoea Number of hrs between challenge and onset | Duration (hours) | Mortality | Weight 24 hours after challenge |
|---|---|---|---|---|---|---|---|
| 2 | A | 2-10 | LT | — | — | — | no change |
|   |   | 2-11 | LT | — | — | — | + 3.5% |
|   |   | 2-12 | LT | — | — | — | + 9.5% |
|   |   | 2-13 | LT | — | — | — | no change |
|   |   | 2-14 | ST | — | — | — | + 3.6% |
|   |   | 2-15 | ST | — | — | — | no change |
|   |   | 2-16 | ST | — | — | — | + 2.8% |
| 3 | A | 3-17 | LT | — | — | — | + 10.6% |
|   |   | 3-18 | LT | — | — | — | + 11.8% |
|   |   | 3-19 | LT | — | — | — | + 6.3% |
|   |   | 3-20 | LT | — | — | — | + 5.8% |
|   |   | 3-21 | ST | — | — | — | + 10% |
|   |   | 3-22 | ST | — | — | — | + 11.9% |
|   |   | 3-23 | ST | — | — | — | + 10.4% |
|   |   | 3-24 | ST | — | — | — | + 7.5% |
| 10 (control) | — | 10-01 | LT | 6 | 24 | — | − 10% |
|   |   | 10-02 | LT | 6-12 | 24 | — | − 10.9% |
|   |   | 10-03 | LT | 6 | 12 | — | − 5.3% |
|   |   | 10-04 | LT | 6 | 96 | + | − 14.7% |
|   |   | 10-05 | LT | 6-12 | 10 | — | − 7.6% |
|   |   | 10-06 | ST | — | — | — | no change |
|   |   | 10-07 | ST | 1 | 3 | — | no change |
|   |   | 10-08 | ST | — | — | — | no change |
|   |   | 10-09 | ST | 6 | 12 | — | no change |

TABLE 2

| SOW N° | Vaccinated with | PIGLET N° | Challenged with | Diarrhoea Duration (hours) | Mortality | Weight 24 hours after |
|---|---|---|---|---|---|---|
| 47 | A | 47-12 | LT | — | — | no change |
|   |   | 47-13 | LT | — | — | + 9.2% |
|   |   | 47-14 | LT | — | — | no change |
|   |   | 47-15 | LT | — | — | + 6.4% |
|   |   | 47-16 | LT | — | — | + 6.6% |
| 48 | B | 48-08 | LT | — | — | + 5.2% |
|   |   | 48-09 | LT | — | — | + 6.7% |
|   |   | 48-10 | LT | — | — | + 3.7% |
|   |   | 48-11 | LT | — | — | + 10.5% |

TABLE 2-continued

| SOW | | PIGLET | | | | |
|---|---|---|---|---|---|---|
| | Vacci- | | Chal- | Dura- | Mor- | |
| | nated | | lenged | tion | tal- | Weight 24 |
| N° | with | N° | with | (hours) | ity | hours after |
| | | 50-01 | LT | 5 | 21 | + | −19.8% |
| | | 50-0.2 | LT | — | — | — | no change |
| 50 | — | 50-03 | LT | — | — | — | + 2.6% |
| (control) | | 50-04 | LT | 6 | 14-21 | + | − 22.1% |
| | | 50-05 | LT | 14 | 48 | + | − 18.8% |
| | | 50-06 | LT | 21 | 10 | — | − 3.2% |
| | | 50-07 | LT | 6 | 21 | + | − 28.5% |

TABLE 3

| SOW | | PIGLET | | | | |
|---|---|---|---|---|---|---|
| | Vacci- | | Chal- | Dura- | Mor- | |
| | nated | | lenged | tion | tal- | Weight 24 |
| N° | with | N° | with | (hours) | ity | hours after |
| | | 13-119 | LT | — | — | — | + 8.4% |
| | | 13-120 | LT | — | — | — | + 11.4% |
| | | 13-121 | LT | — | — | — | + 2 |
| | | 13-122 | LT | — | — | — | no change |
| 13 | B | 13-123 | LT | — | — | — | + 7.1% |
| | | 13-124 | LT | 4 | 2 | — | + 8.1% |
| | | 13-125 | LT | — | — | — | + 8% |
| | | 13-126 | LT | — | — | — | + 5.8% |
| | | 13-127 | LT | 8 | 10 | + | − 21% |
| | | 13-128 | LT | — | — | — | + 8.4% |
| | | 21-110 | LT | 3 | 48 | + | −15% |
| | | 21-111 | LT | 3 | 6-11 | — | − 6.9% |
| | | 21-112 | LT | 4 | 48 | + | − 14.3% |
| 21 | C | 21-114 | LT | — | — | — | − 5.9% |
| x | | 21-115 | LT | 6 | 6 | — | − 6.3% |
| | | 21-116 | LT | — | — | — | − 3.6% |
| | | 21-117 | LT | — | — | — | − 2% |
| | | 21-118 | LT | 6 | 5 | — | −12.5% |
| | | 15-129 | LT | — | — | — | + 7.4% |
| | | 15-130 | LT | — | — | — | + 4.9% |
| 15 | C | 15-131 | LT | — | — | — | + 13.2% |
| | | 15-132 | LT | — | — | — | + 16% |
| | | 15-133 | LT | — | — | — | no change |
| | | 20-101 | LT | 5 | 6 | — | − 3.6% |
| | | 20-102 | LT | 6 | 6 | — | − 16.5% |
| | | 20-103 | LT | 25 | 4 | — | − 4.5% xx |
| | | 20-104 | LT | 19 | 6 | — | − 5.3% |
| 20 | —20-105 | LT | 6 | 6 | — | | 4.7% |
| (control) | | 20-106 | LT | 3 | 4-9 | — | no change |
| | | 20-107 | LT | — | — | — | − 3.2% |
| | | 20-108 | LT | 6 | 6 | — | − 5.7% |
| | | 20-109 | LT | 6 | 6 | — | − 4.2% | x Mastitis appeared 48 hours after farrowing;
xx Loss of weight 4 hours after appearance of diarrhoea.

The results of the trials show that six out of the seven litters from vaccinated sows were protected against oral challenge with *E. coli* enterotoxins. The afforded protection was 90 % for 1 litter and 100 % for the five other ones. No litter of the control sows showed resistance to the same challenge with enterotoxins while the mortality and morbidity among the control piglets ranged from 71.4 to 88.8 %.

In five out of seven litters from vaccinated sows, all piglets were completely protected; in one litter, eight out of 10 piglets were completely protected. In the piglets challenged with LT enterotoxin and derivated from control sows, the figures were as follows : in one litter, five out of five animals showed typical symptoms; in another litter five out of seven and in the third litter eight out of nine.

EXAMPLE 7

A 12 g aliquot of freeze-dried enterotoxin preparation obtained according to the process described in example 1 is suspended in 1 liter of pyrogen free distilled water and the suspension is mixed with a solution of 20 g of ALHYDROGEL (a product manufactured and sold by SUPERFOS EXPORT Company) in 1 liter of pyrogen free distilled water. The pH is adjusted to 6 with N hydrochloric acid and the mixture is allowed to stand in the dark at room temperature for 40 hours with intermittent stirring in order to allow adsorption of the enterotoxing on ALHYDROGEL. The final pH is 6.3.

After centrifugation, the supernatant is discarded and the sediment is re-hydrated by addition of 2.2 l. of a 50/50 mixture of physiological serum and buffer (22 g. $Na_2HPO_4$(M/10) and 78 g. $KH_2PO_4$(M/10) with 10 mg. of thiomersal for 100 ml.; pH 6.3).

The mixture is stirred at 4° C for 2 hours and divided into two 1100 ml. batches, respectively named A and B. Batch A (which contains 5.4 mg. of enterotoxin preparation and 9 mg. of ALHYDROGEL per ml.) is divided into 5 ml. aliquots (thus containing 27 mg of enterotoxin preparation) which are distributed into glass vials which are then sealed. Batch B is diluted by addition of 303 ml. of a 50/50 mixture of physiological serum and buffer (22 g. $Na_2HPO_4$ (M/10) and 78 g. $KH_2PO_4$ (M/10) with 10 mg. of thiomersal for 100 ml.; pH 6.3) supplemented with 2.7 g. of ALHYDROGEL. Batch B (which contains 4.3 mg. of enterotoxin preparation and 9 mg. ALHYDROGEL per ml.) is divided into 2.5 ml. aliquots (thus containing 10.75 Mg of enterotoxin preparation) which are distribution into glass vials which are then sealed.

The vaccine preparation of batches A and B have been tested as follows on sows in breeding centers contamined by colibacillary diarrhoea.

Therefore the sows were subcutaneously inoculated between 3 and 6 weeks before farrowing with one single dose of vaccine : 59 sows receiving one dose of batch A vaccine and 28 sows receiving one dose of batch B vaccine. Fifty sows were used as control receiving the same volumes of the same ALHYDROGEL/buffer mixture without enterotoxin extract.

All piglets were observed for the appearance of diarrhoea.

On and after the second day of clinical symptom of illness, the piglets were treated by daily administration of chloramphenicol, ampicillin or sulfadoxin/trimethoprim.

The results are summarized in the following Table 4 taking into account feces consistance duration of diarrhoea, numberof antibiotic administrations and mortality by dehydration.

TABLE 4

| Vaccine dose | Total number of litters | Number of litters showing severe diarrhoea (x) | Percentage of litters showing severe diarrhoea (x) | Number of litters with mortality | Percentage of litters with mortality |
|---|---|---|---|---|---|
| 5 ml. of batch A | 59 | 15 | 25.4 | 2 | 3.3 |
| 2.5 ml. of batch B | 8 | 10 | 35.7 | 2 | 7-1 |
| placebo (xx) | 50 | 24 | 48 | 8 | 16 |

(x) i.e. liquid feces for more than two days, several antibiotic administrations, with and without mortality.
(xx) a group of 25 sows receiving 2.5 ml. and the other group of 25 sows receiving 5 ml.

The results of Table 4 indicate that theadministration of vaccines acccording to the invention considerably reduces the percentage of illness and mortality, better protection being obtained after administration of the 27 mg. enterotoxin dosage unit to the sows.

We claim:

1. A pre-farrowing pregnant sow piglet colibacillosis vaccine for intramuscular or subcutaneous administration to pregnant sows 3 to 6 weeks before farrowing comprising a unit dosage or multidose integer of the dosage of an effective amount of at least 5 to 150 mg. lipopolysaccharide- and cell-free heat labile (LT) *E. coli* enterotoxin isolated from a culture of an *E. coli* serotype which is capable of causing piglet colibacillosis and protective against the actions of heat stable and heat labile enterotoxins produced by heterologous as well as homologous enteropathogenic *E. coli* serotypes, and an effective amount of an adjuvant selected from the group consisting of aluminium hydroxide, aluminium phosphate, peanut oil emulsified by the addition of monooleate and stabilized by the addition of aluminium monostearate or Freund's adjuvant.

2. A piglet colibacillosis vaccine according to claim 1, wherein the *E. coli* enterotoxin is isolated from *E. coli* strain ATCC 21972.

3. A piglet colibacillosis vaccine according to claim 1, wherein the adjuvant is Freund's adjuvant.

4. A piglet colibacillosis vaccine according to claim 1, wherein the adjuvant is aluminium gel.

5. A piglet colibacillosis vaccine according to claim 2, wherein the dose of enterotoxin is at least 27 mg.

6. A piglet colibacillosis vaccine according to claim 5, wherein the adjuvant is aluminium gel.

7. A method of preventing piglet colibacillosis comprising administering to pregnant sows from 3 to 6 weeks before farrowing a vaccine according to claim 1.

8. A method of preventing piglet colibacillosis comprising administering to pregnant sows from 3 to 6 weeks before farrowing a vaccine according to claim 6.

* * * * *